United States Patent
Kidwell

(10) Patent No.: US 9,646,803 B2
(45) Date of Patent: May 9, 2017

(54) TRANSMISSION ELECTRON MICROSCOPY SUPPORTS AND METHODS OF MAKING

(71) Applicant: The United States of America, as represented by the Secretary of the Navy, Washington, DC (US)

(72) Inventor: David A. Kidwell, Alexandria, VA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 15/073,296

(22) Filed: Mar. 17, 2016

(65) Prior Publication Data

US 2016/0329187 A1    Nov. 10, 2016

Related U.S. Application Data

(60) Provisional application No. 62/157,866, filed on May 6, 2015.

(51) Int. Cl.
| | |
|---|---|
| *H01J 37/20* | (2006.01) |
| *H01J 37/26* | (2006.01) |
| *C23C 16/01* | (2006.01) |
| *C23C 16/40* | (2006.01) |
| *G01N 1/28* | (2006.01) |

(52) U.S. Cl.
CPC ............ *H01J 37/26* (2013.01); *C23C 16/01* (2013.01); *C23C 16/403* (2013.01); *G01N 1/28* (2013.01); *H01J 37/20* (2013.01)

(58) Field of Classification Search
CPC .......... H01J 37/26; H01J 37/20; H01J 37/244; B82Y 10/00; B82Y 30/00; B82Y 40/00
USPC ........... 250/311, 440.11, 307, 309, 310, 398; 216/2, 24, 56
See application file for complete search history.

(56) References Cited

U.S. PATENT DOCUMENTS

| | | | | |
|---|---|---|---|---|
| 7,482,587 | B1 * | 1/2009 | Finch | H01J 37/20 216/2 |
| 8,212,225 | B2 * | 7/2012 | Hutchison | H01J 37/20 216/24 |
| 8,920,723 | B2 * | 12/2014 | Damiano, Jr. | G01N 23/046 356/369 |
| 2012/0160999 | A1 * | 6/2012 | Zaluzec | H01J 37/244 250/307 |

* cited by examiner

*Primary Examiner* — David A Vanore
(74) *Attorney, Agent, or Firm* — US Naval Research Laboratory; Stephen T. Hunnius

(57) ABSTRACT

A method of making a Transmission Electron Microscopy support comprising depositing a sacrificial layer to the top side of a lacey or holey carbon structure or support or wire mesh, depositing an Atomic Layer Deposition layer to the bottom side of the sacrificial layer, removing the sacrificial layer, forming a Transmission Electron Microscopy support. The Transmission Electron Microscopy support comprises an Atomic Layer Deposition layer which is carbon-less, thin, flexible, can be thermally cleaned, can be plasma cleaned, and contains chemical functionalities to immobilize particles.

12 Claims, 10 Drawing Sheets

TRANSMISSION ELECTRON MICROSCOPY SUPPORTS AND METHODS OF MAKING

This application claims priority to and the benefits of U.S. Patent Application No. 62/157,866 filed on May 6, 2016, the entirety of which is herein incorporated by reference.

BACKGROUND

Electron Microscopy grids are used as supports for observing nanoparticles and biological molecules. Scanning Electron Microscopy (SEM) looks at the electrons scattered from the front of a sample and thus can observe thick samples. As opposed to SEM, Transmission ElectronMicroscopy (TEM) works by passing the electron beam though the sample AND the support. There are two types of TEMs—High-Resolution TEM (HRTEM or often abbreviated just TEM) and Scanning Transmission Electron Microscopy (STEM). In HRTEM, the electron beam is parallel at the sample. Contrast is obtained by changing the phase of the electrons and their interference with each other. In another form of TEM, Scanning TEM (STEM), the electron beam is focused at the surface to a fine spot. Contrast is obtained by scattering of the electrons from the atoms. The heaver the atom, the more the scattering. Electrons that do not scatter are often not analyzed.

In both HRTEM and STEM, since the electrons must pass though the support, the thinner the support the less contrast the support contributes to the total image. For the observation of particles <1 nm in diameter, i.e. a few atom layers thick, the ideal support would be vacuum. However, vacuum does not immobilize the particles, so atoms in the nanoparticle cannot often be imaged because they move and blur during the analysis.

Recently, graphene and graphene oxide supports have become commercially available as examples of thin supports being only one atom thick in ideal cases. However, these supports are often contaminated with carbon from either the preparation process or storage in air. This added carbon adds noise to the image due to its random nature. Additionally, graphene, being only one atom thick, is not robust from handling during sample deposition nor the electron beam during analysis. Thus, Ultrathin Carbon (UT) Type A (3-4 nm) with removable Formvar thick film of amorphous carbon is often employed to image nm size samples. UT carbon is typically prepared by evaporating carbon onto a flat surface such as mica, removing the mica by separating with water, and floating the UT carbon onto a grid or grid with a support. UT carbon has limitations in that it cannot be readily cleaned. Additionally, being carbon, the carbon is transferred to the sample during analysis by the electron beam, which changes the structure of the sample.

Silicon monoxide supports are commercially available but they are too thick for good HRTEM work. Additionally, they are not available commercially as supported films, so they previously could not be made very thin—until this invention solved this long standing problem.

BRIEF SUMMARY OF THE INVENTION

A very robust and flexible TEM support that contains functionalities to immobilize nanoparticles, and methods of making.

DETAILED DESCRIPTION

This invention provides a very robust and flexible TEM support that contains functionalities to immobilize nanoparticles and methods of making.

These new TEM supports can be cleaned by plasma treatment, which allows removal of carbon contamination, often introduced during sample application, which obscures small nanoparticles. They can be made carbon-less, which avoids deposition of carbon from conventional ultra-thin carbon supports during scanning transmission electron microscopy (STEM). They allow EDAX if one is looking for carbon and provide various matrices in case one support interferes with the element sought.

These new TEM supports provide chemical functionality to fix particles. They are robust and not readily damaged by the electron beam. They are amorphous or contain amorphous areas for tuning the TEM.

Example 1

Figure 1:
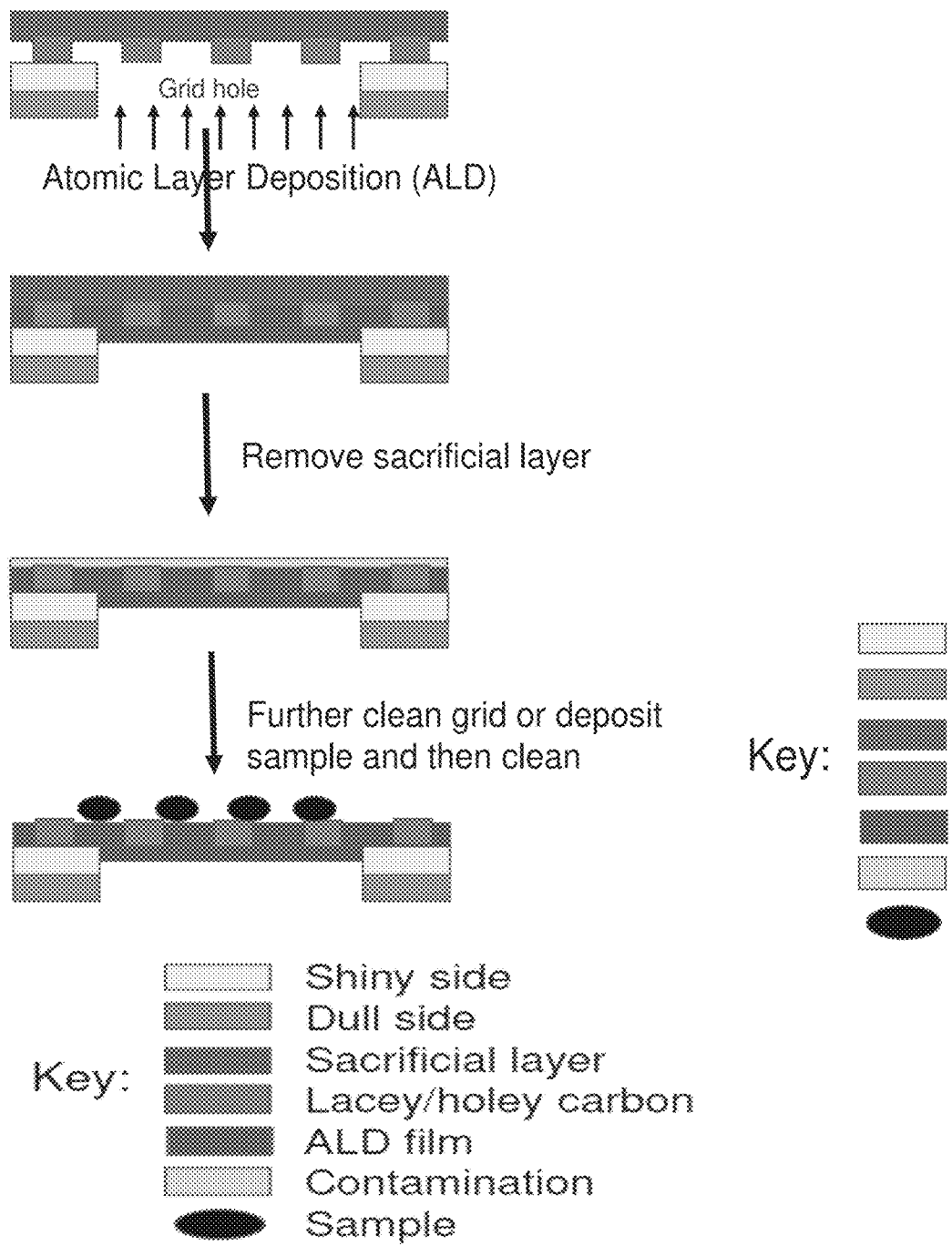
FIG. 1 illustrates steps in the preparation of thin, oxide grids.
Figure 2:
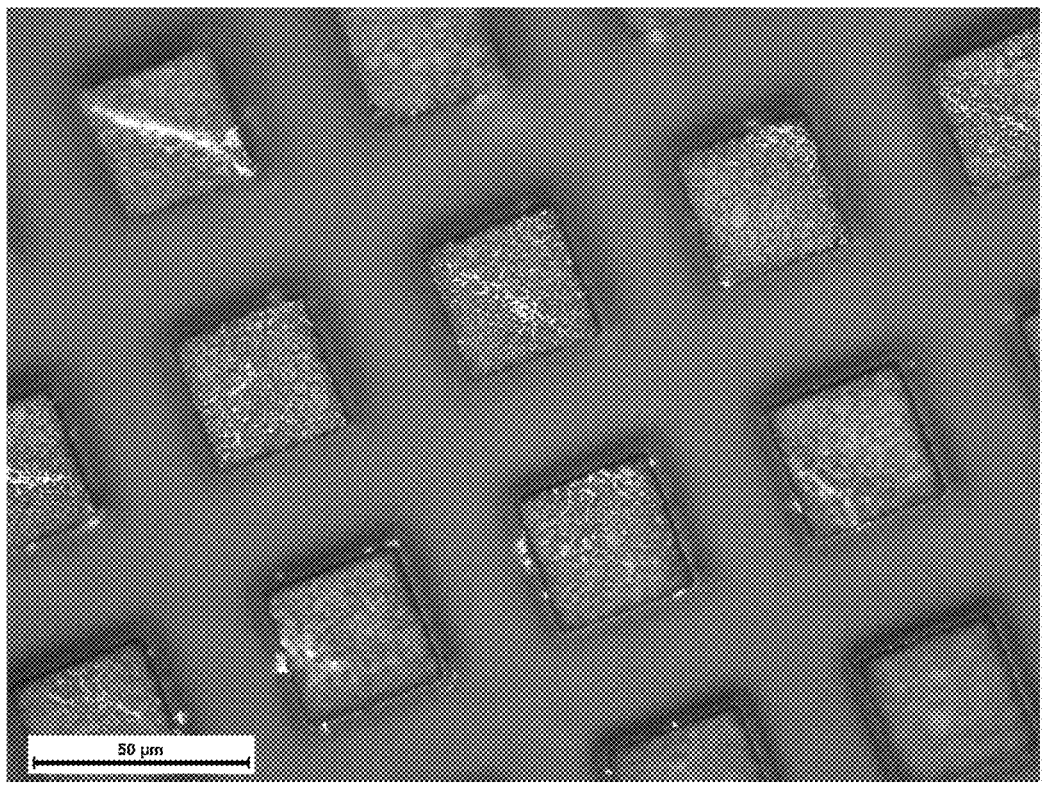
FIG. 2 is an optical micrograph of a grid showing the holey carbon support. There is an approximately 1 nm film of alumina spanning most/all of the transparent parts of the grid.

Referring to FIG. 1, the key aspect in the first step is to have a sacrificial support film to grow the ALD film onto. The support film may span the hole of a TEM grid or be further supported by lacey or holey carbon. Lacey or holey carbon provides micro and sub-micron holes that span the TEM grid (see FIG. 2) and act as a support and electron conduction path for very thin and insulating supports, such as prepared in the instant disclosure.

Suitable commercial support film TEM grid can be used. Some examples include Ted Pella Cat #01702 (Formvar coated 400 mesh copper grids), Ted Pella Cat #01822 (Ultrathin Carbon Type A (3-4 nm) with Removable Formvar on 400 mesh copper grids), Ted Pella Cat #1829 (Silicon Monoxide with removable Formvar on 300 mesh copper grids), Ted Pella Cat #21710-5 (Single layer graphene on lacey carbon on 300 mesh copper grids), Ted Pella Cat #21810-5 (Single Layer Graphene Oxide TEM Support Films on Lacey Carbon, 300 Mesh Copper Grids), Ted Pella Cat #01824 or #01824G (Ultrathin Carbon (<3 nm) on Carbon Holey Support Film on 300 mesh copper or gold grids). Cat #01824 being preferred and Cat #01824G being most preferred as both have the supporting holey carbon. The gold grid is preferred because it survives heating in air or oxygen to remove residual carbon from the produced support film. Copper oxidizes during this step and catalyzes the growth of alumina needles (see below). The thickness of the sacrificial film is not critical as it is removed and thus does not impact the electron beam in the TEM. As the ALD makes a replica of the sacrificial film and any contamination present, the smoothness and cleanliness is an important aspect.

Example 2

After selection of the grid, the back is coated using atomic layer deposition (ALD) though techniques known in the art. The thickness of the layer varies with the number of ALD cycles. For an approximately 1 nm thick alumina film, 10 cycles is used. For an approximately 2 nm thick alumina film, 20 cycles are employed. Either thickness will span a 400 mesh grid holes and survive deposition of nanoparticle solutions. However, the 1 nm film is unstable to an electron beam, presumably due to charging, so that reliable TEM data could not be obtained. The 2 nm grid was stable if covering the complete hole in the grid, but edges charges and curled. Little of these problems were evident for holey or lacey carbon supported grids.

Example 3

Figure 3:
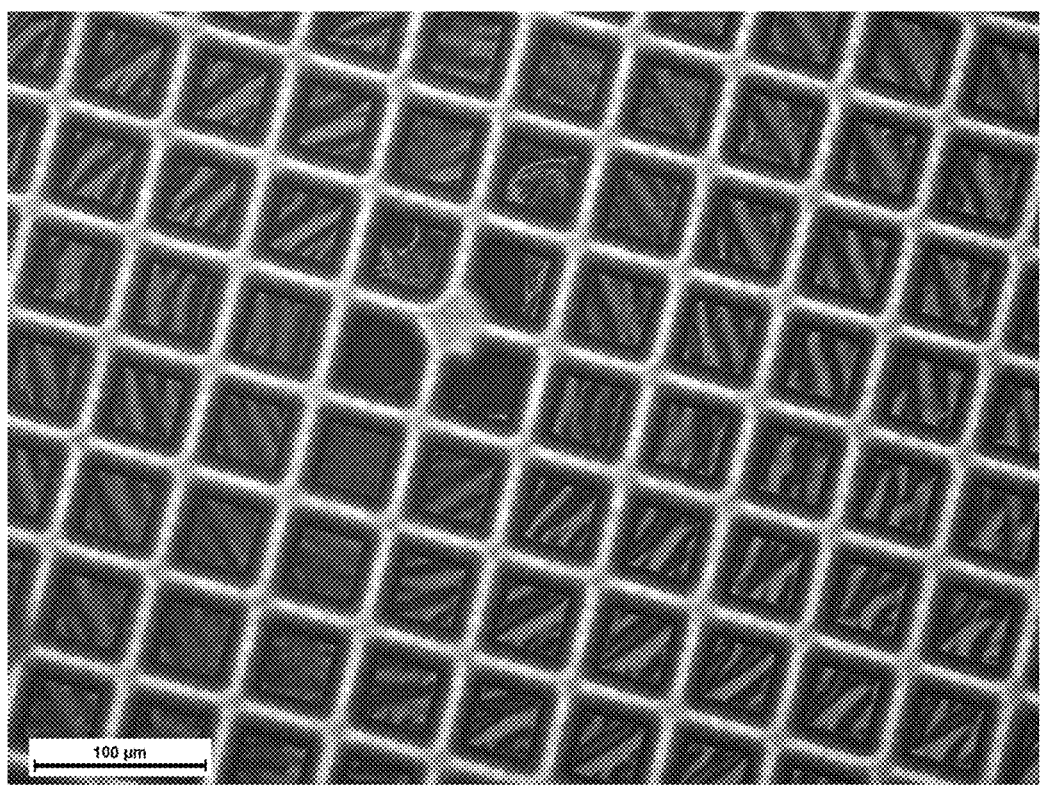
FIG. 3 is an optical micrograph of a grid after alumina ALD over Formvar. Some of the roughness is due to contamination on the Formvar. This picture is before the sacrificial Formvar is removed and most holes are filled. The three holes in the middle have the film broken. No holey/lacey carbon support is present so that the film is somewhat fragile after the Formvar is removed.
Figure 4:
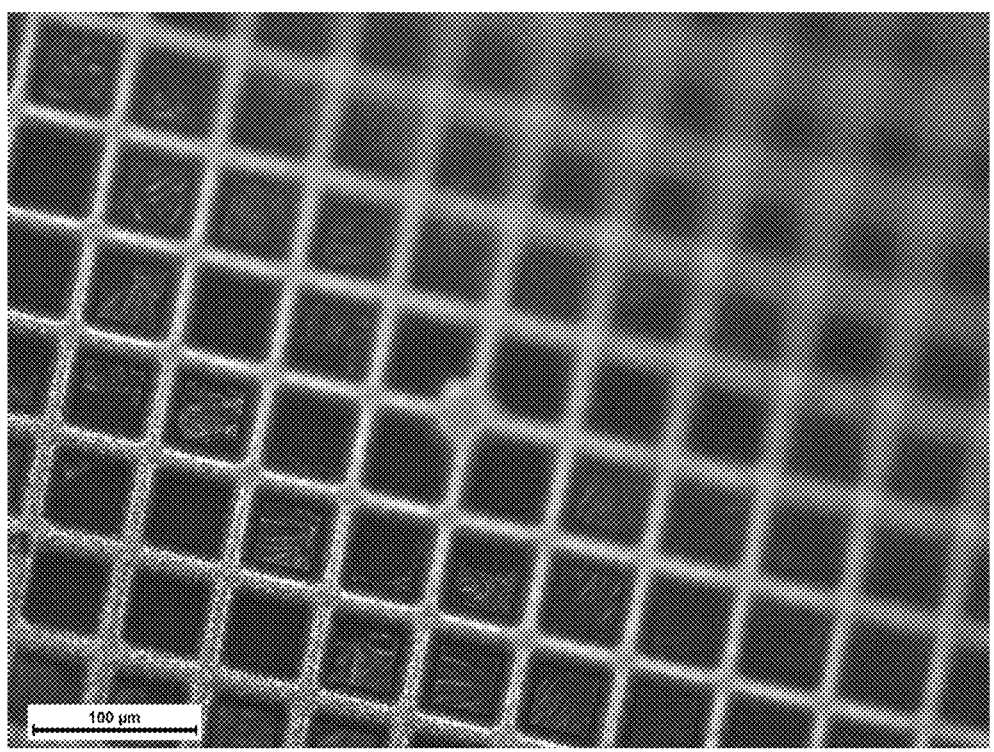
FIG. 4 is an optical micrograph of a grid showing unsupported alumina film covering several of the holes in the grid. This film is approximately 2 nm thick yet can span a 63 μm hole. Some of the roughness is due to the roughness of the sacrificial film that the ALD makes as a replica. The sacrificial film of Formvar was removed with chloroform for this grid.

After the ALD deposition, the sacrificial layer is removed by suitable techniques. For Formvar only supports (FIG. 3), solvents such as chloroform or ethylene dichloride are suitable. FIG. 4 shows an unsupported film with the Formvar removed. For ultra-thin carbon, a 40 min oxygen plasma is suitable. For silicon monoxide, exposure to a solution of ammonium fluoride in water (160 mg/7.7 mL) overnight removes the silicon monoxide and retains the alumina.

Example 4

The TEM grids may then be coated with nanoparticles in the normal matter by dipping into aqueous or organic solutions of the nanoparticles or drop drying of the solutions onto the surface. After particle application, residual carbon may be removed by $O_2$/Ar plasma treatment or heating at 350° C. in air. For heating, gold grids are preferred as they resist oxidation. For small gold nanoparticles, plasma treatment is preferred to avoid coalescence of the particles.

By making thin supports out of oxide materials such as alumina, SiN, SiOx, BN, or mixtures thereof, this invention overcomes many of the limitations of commercial supports.

The present invention provides TEM grids that are thin. Being thin is important for good TEM results.

The present invention provides TEM grids that can be cleaned by plasma treatment, which allows removal of carbon contamination that obscures small nanoparticles. Often times, solution deposition of particles also deposits other contaminates. Plasma cleaning is one way to remove these contaminates but such an aggressive technology also destroys the prior art supports that are commercially available.

The present invention provides TEM grids that can be thermally cleaned. Being oxides, they can be heated to high temperatures in air (or oxygen) to thermally remove contaminants or oxidize them.

The present invention provides TEM grids that can be made carbon-less, which avoids deposition of carbon from conventional ultra-thin carbon supports during STEM.

The present invention provides TEM grids which allow alternative elements for EDAX if one is analyzing for carbon.

The TEM grids of the current invention provide various matrices in case one support interferes with the element sought. For example, trying to determine carbon inclusion in steel is difficult if carbon is present. Alternatively, studying aluminum would necessitate use of a SiN or BN support.

The TEM grids of the current invention provide chemical functionality to fix particles which slows or stops their coalescence during the TEM analysis. Many nanoparticle migrate on a surface under the influence of the electron beam. Having oxygen functionalities (in the case of alumina or SiOx), amines (possible with SiN), or B oxides (possible in the case of BN), allow atomic handles for the nanoparticles to interact and bond. This is not possible with graphene or UT carbon.

Additionally, mixed oxides are possible for unique applications such as studying the effect of catalyst supports on the structure of catalytic nanoparticles (especially in environmental TEM).

Another benefit of the present invention is that it provides TEM grids that are robust and not readily damaged by the electron beam.

Furthermore, another benefit of the current invention is TEM grids that are amorphous or contain amorphous areas for tuning the TEM. TEM requires Thon rings for correcting the aberrations. Thon rings can only be generated by amorphous substances—either the support or the support backing (i.e. typically lacy or holey carbon).

Other grids are being micro machined from silicon nitride but these are typically 2 nm thick and are very expensive. Additionally, the area is very limited and SiN is not very conductive so the samples charge and reduce the resolution. Additionally, SiN is not stable to oxidation but can be to thermal treatment.

The current invention uses thin alumina films for TEM grids to perform the atomic layer deposition (ALD) as ALD provides the most precise means for control of film thickness. Alternative film deposition techniques such as molecular beam epitaxy or sputtering can also be employed as they can provide a wider mix of materials.

This technology solves several problems in current TEM and will make less expensive, more flexible, and more robust supports than are currently available.

For example, the present invention provides TEM grids that are thin and robust and can be cleaned by plasma treatment, which allows removal of carbon contamination that obscures small nanoparticles. The present invention provides TEM grids that can be thermally cleaned and can be made carbon-less.

Additionally, the TEM grids of the current invention provide chemical functionality to fix particles. Many nanoparticle migrate on a surface under the influence of the electron beam. Having oxygen functionalities (in the case of alumina or SiOx), amines (possible with SiN), or B oxides (possible in the case of BN), allow atomic handles for the nanoparticles to interact and bond. This is not possible with graphene or UT carbon.

Example 5

Preferred preparation techniques for these grids start with commercially available materials. However, alternative preparation techniques can be used. For example, start with a flat surface such as freshly cleaved mica. Add a release layer such as evaporated carbon or a polymer. Coat the release layer with the thin film. Release the carbon from the mica by dipping in water to float the film onto the water surface. Attach the film to a grid by either placing on top of the film, bringing the grid from underneath, or slowing draining the water onto a grid.

This procedure offers an advantage in providing a flatter film over larger areas as the oxide would not be as conformal to the grid but requires transferring fragile films to the grid.

Example 6

Another example is how Formvar grids are made by either casting the Formvar onto a glass slide and floating onto water or casting directly onto the water. Then attaching the grids as in the case of UT carbon. For ALD, other liquids may be substituted for water to provide a flat surface. An example maybe wax or a liquid metal, depending on the temperature of the ALD process and the exact chemistry.

Example 7

The preferred method has the advantage of coating the lacy or holey carbon support with the oxide film and protecting it for degradation during cleaning. The lacy or holey carbon provides support for the film and conductive paths for the electrons to reduce charging of the film, which reduces the resolution of the TEM. Alternatively coat the lacy or holey carbon with an oxide before attaching the film but this is an extra step. Supports are available coated with silicon monoxide, which is typically too thick but could be made thinner and more controlled by using ALD.

Example 8

Nanoparticles on ultra-thin carbon are unstable to the electron beam and will quickly coalesce. Having functionalities present that pin the nanoparticles allow for their easy imaging via HRTEM.

Figure 5:
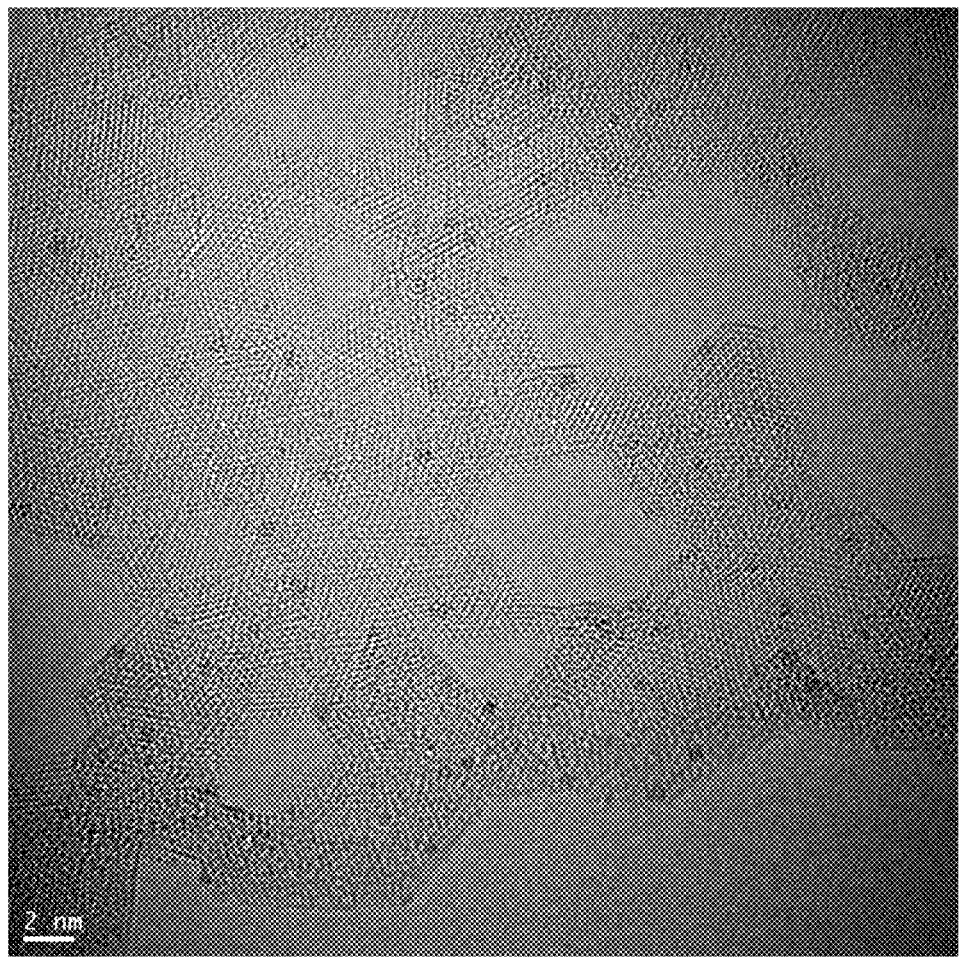
FIG. 5 shows a TEM image of gold clusters on ALD alumina made with the present invention using 10 cycles of ALD. The membrane is less than 1 nm thick.
Figure 6:
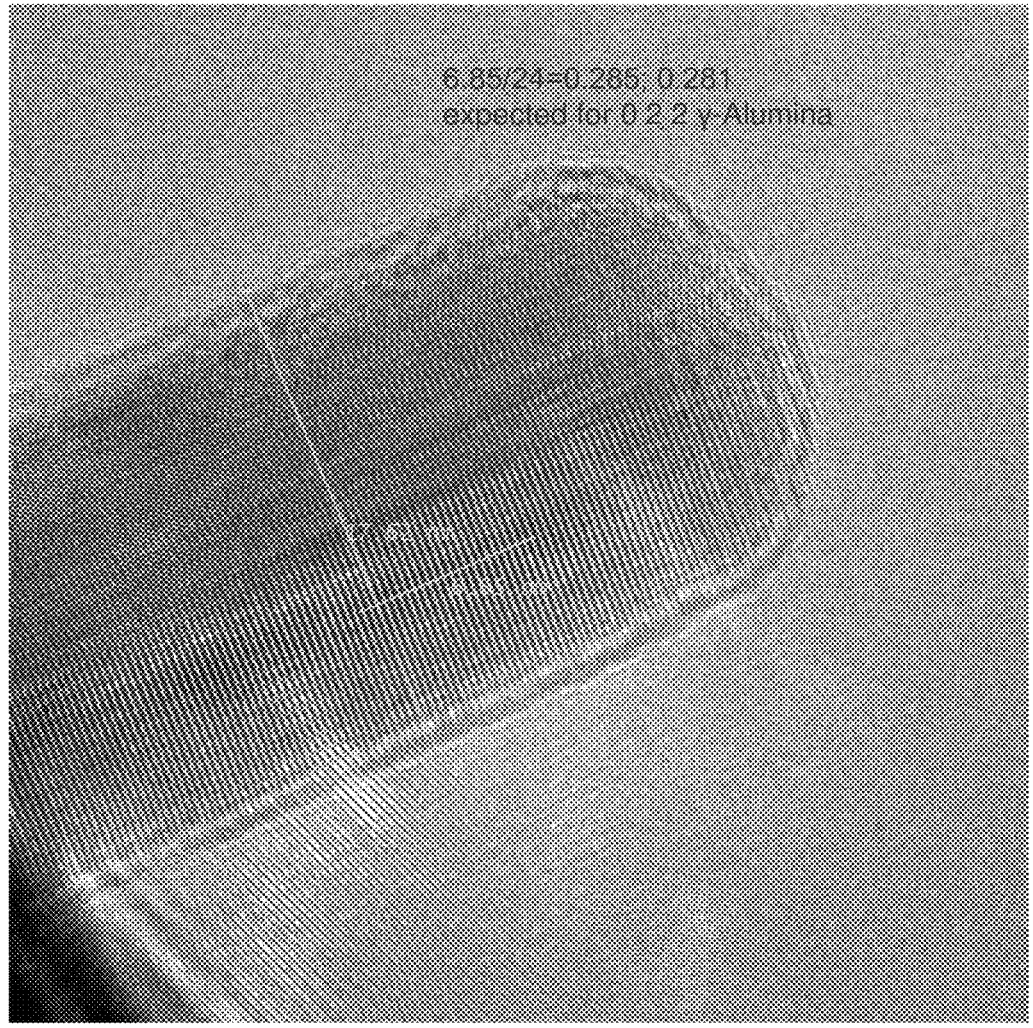
FIG. 6 shows a high-resolution TEM image of a single alumina needle made with the present invention showing the lattice spacing. The lattice spacing of 0.281 nm is representative of gamma-alumina crystals.
Figure 7:
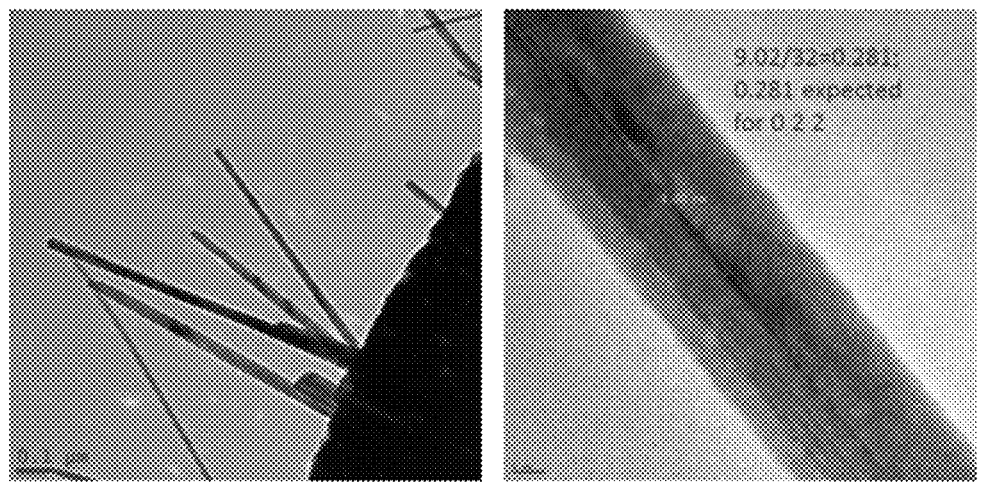
FIG. 7 shows growth of alumina needles from the side of a copper TEM grid after cleaning of an ALD film at 350° C. in air for 15 min. Growth appears to be catalyzed by copper and the growth may thin the alumina substrate even further. No needles grow on gold grids.
Figure 8:
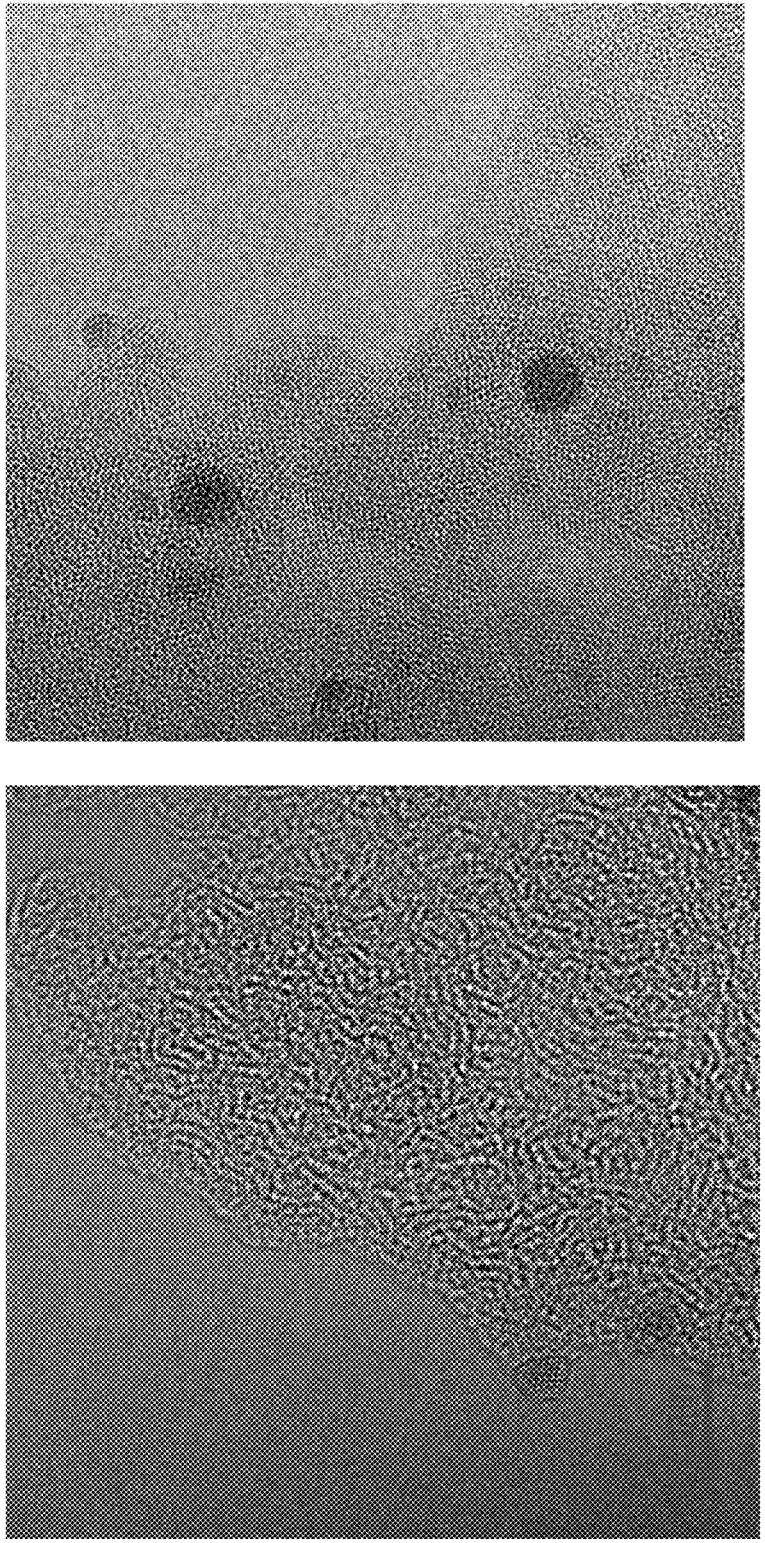
FIG. 8 shows high-resolution TEM images of commercially-available gold nanoparticles (mixture of Nanogold® and Undecagold—Nanoprobes, Inc., Yaphank N.Y.) before and after argon plasma cleaning and then heating in air. The gold nanoparticles are difficult to observe due to the carbon shells protecting them from coagulation. The aggressive cleaning procedure removes the carbon shells yet the nanoparticles do not coagulate due to binding to the surface.
Figure 9:
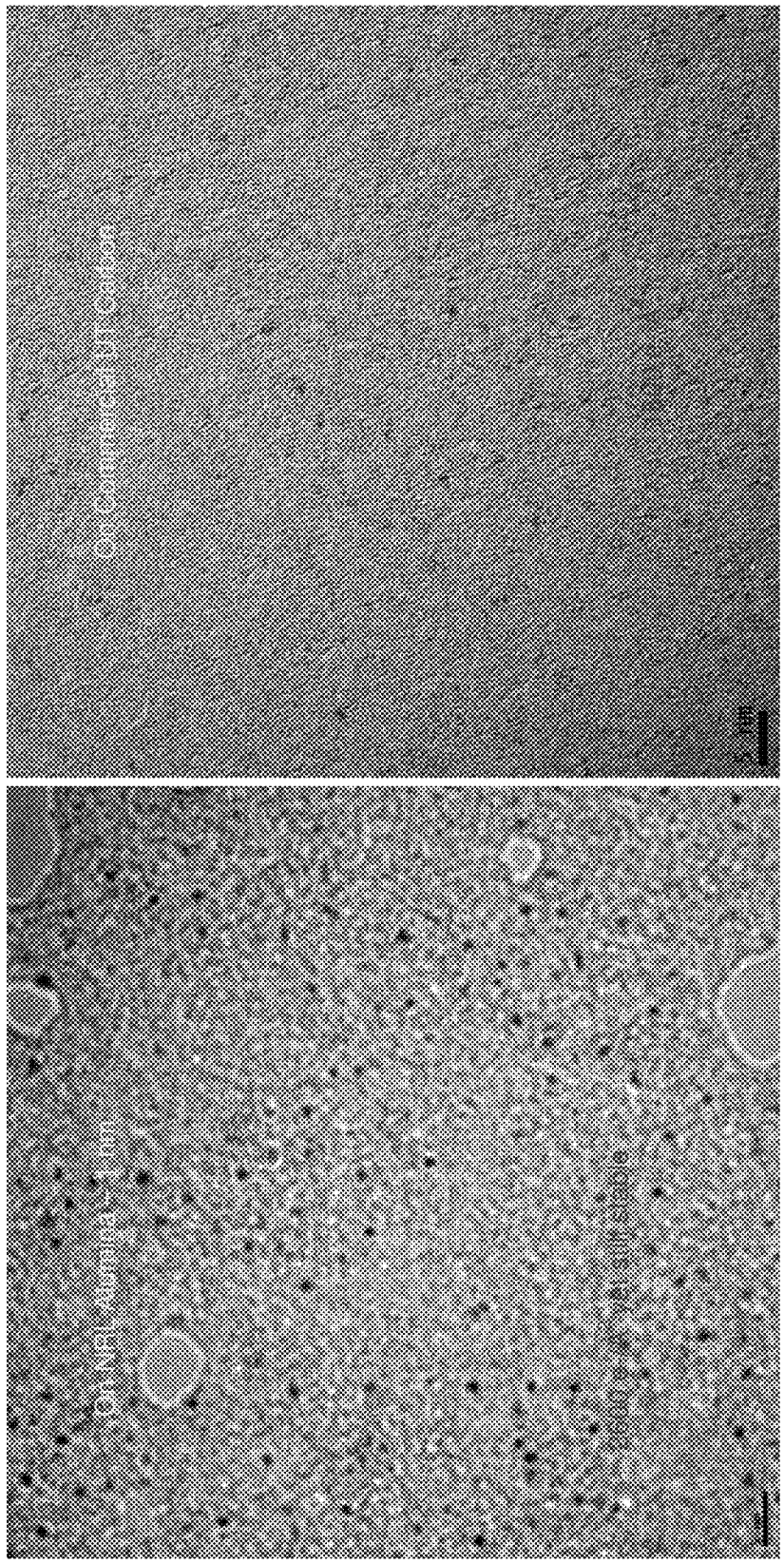
FIG. 9 shows high-resolution TEM images of Undecagold nanoparticles on an alumina TEM support made with the present invention and on commercial ultra-thin carbon. The alumina provides much better resolution likely because it is thinner.
Figure 10:
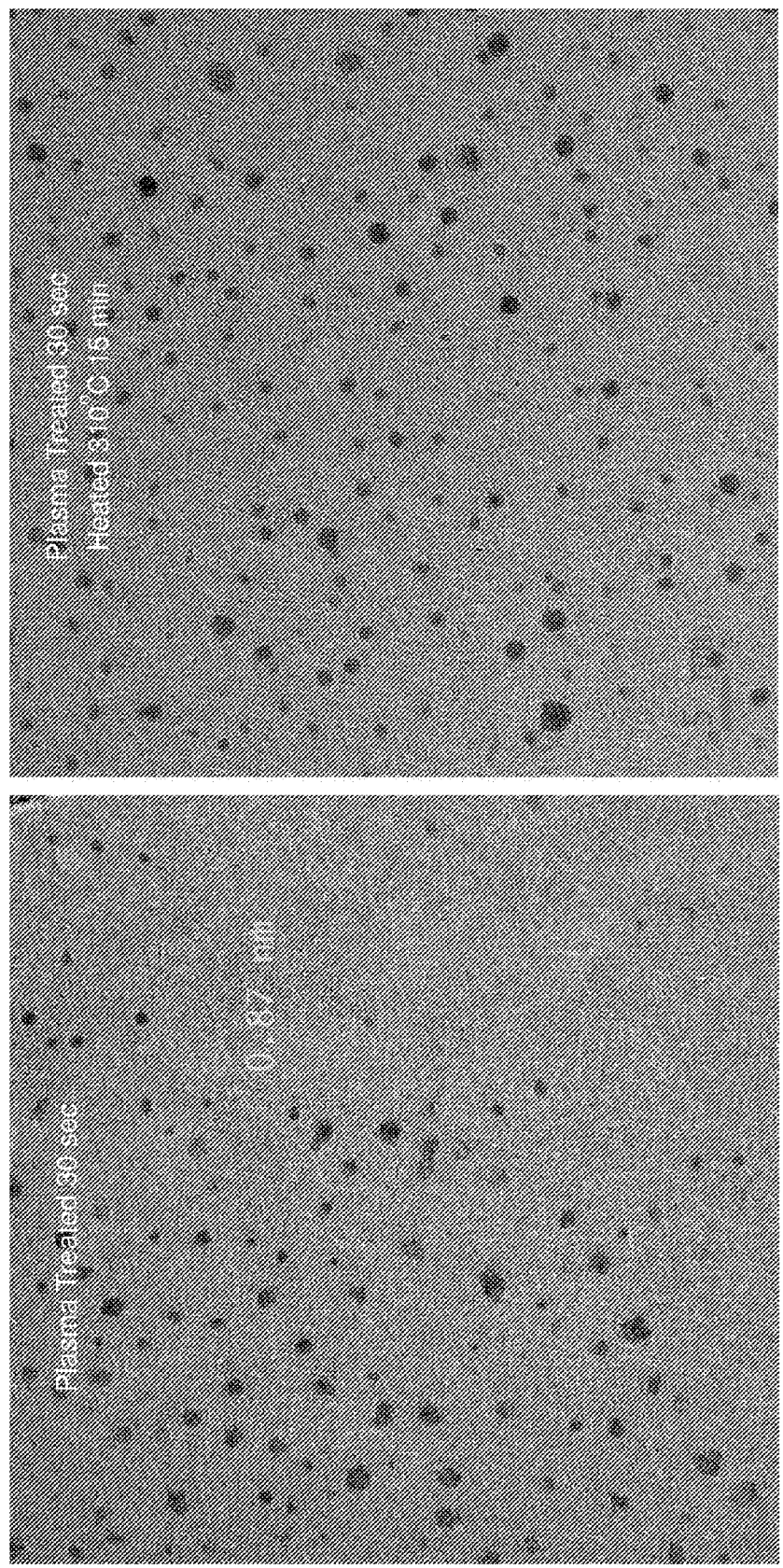
FIG. 10 depicts high-resolution TEM images of commercially-available gold nanoparticles (Undecagold—Nanoprobes, Inc., Yaphank N.Y.) on alumina supports made with the present invention and after argon plasma cleaning and then further heating in air. The aggressive cleaning procedure removes the carbon shells yet the nanoparticles do not coagulate due to binding to the surface nor does the support degrade.

As an example, small clusters of gold atoms (4-8 atoms) are shown in FIG. 5 on a very thin alumina membrane made by the present invention. The membrane has crystallized under the electron beam into gamma alumina sheets. Each black dot is a gold atom and the aluminum and oxygen atoms of the substrate are clearly visible.

Being able to image single atoms over an extended period shows that they do not move. If the atom did move, the image would be blurry.

This solves several long standing problems in the art.

Many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

I claim:

1. A method of making a Transmission Electron Microscopy support, comprising:
   depositing a sacrificial layer to the top side of a lacey or holey carbon structure or support grid;
   depositing an Atomic Layer Deposition layer to the bottom side of the sacrificial layer; and
   removing the sacrificial layer to form a Transmission Electron Microscopy support.

2. The method of making a Transmission Electron Microscopy support of claim 1, further comprising the step of:
   cleaning the Transmission Electron Microscopy support.

3. The method of making a Transmission Electron Microscopy support of claim 1 wherein the sacrificial layer is one selected from the group consisting of amorphous carbon, formvar, polymer, and silicon monoxide and wherein the Atomic Layer Deposition layer contains functionalities to immobilize nanoparticles.

4. The method of making a Transmission Electron Microscopy support of claim 3 wherein the step of removing the sacrificial layer is performed using a gaseous plasma method of a chemical solvents method.

5. The method of making a Transmission Electron Microscopy support of claim 4 wherein the gaseous plasma is one selected from the group consisting of oxygen, argon, and xenon difluoride.

6. The method of making a Transmission Electron Microscopy support of claim 5 wherein the chemical solvent is one selected from the group consisting of aqueous ammonium fluoride, chloroform, ethylene dichloride, and acetone.

7. The method of making a Transmission Electron Microscopy support of claim 6 wherein the Atomic Layer Deposition layer comprises alumina and wherein the thickness of the Atomic Layer Deposition layer is about 1 nm to about 2 nm.

8. A method of making a Transmission Electron Microscopy support, comprising:
   applying a sample to a Transmission Electron Microscopy support formed by the steps of depositing a sacrificial layer to the top side of a lacey or holey carbon structure or support grid, depositing an Atomic Layer Deposition layer to the bottom side of the sacrificial layer, and removing the sacrificial layer.

9. The method of making a Transmission Electron Microscopy support of claim 8, further comprising the step of:
   cleaning the sample after application to the Transmission Electron Microscopy support.

10. A Transmission Electron Microscopy support, comprising:

an Atomic Layer Deposition layer supported by a lacey or holey carbon structure or support;

wherein the Atomic Layer Deposition layer on the lacey or holey carbon structure was formed by depositing a sacrificial layer to the top side of a lacey or holey carbon structure or support, then depositing an Atomic Layer Deposition layer to the bottom side of the lacey or holey carbon structure, then removing the sacrificial layer and thereby forming a Transmission Electron Microscopy support.

11. The Transmission Electron Microscopy support of claim 10, wherein the Transmission Electron Microscopy support is flexible and contains functionalities to immobilize nanoparticles.

12. A Transmission Electron Microscopy support, comprising:

an Atomic Layer Deposition layer which is carbon-less, thin, flexible, can be thermally cleaned, can be plasma cleaned, and contains chemical functionalities to immobilize particles.

* * * * *